United States Patent [19]

Mackal

[11] Patent Number: 4,602,655
[45] Date of Patent: Jul. 29, 1986

[54] SELF-RETAINING CHECK VALVE AND MOUNTING THEREFOR

[76] Inventor: Glenn H. Mackal, 4923 59 Ave. S., St. Petersburg, Fla. 33702

[21] Appl. No.: 450,453

[22] Filed: Dec. 16, 1982

[51] Int. Cl.[4] .............................................. F16K 15/14
[52] U.S. Cl. .................................... 137/515; 137/540
[58] Field of Search ............... 251/150, 152, 148, 151; 137/515, 515.5, 515.7; 285/381, 382, 382.5; 403/273

[56] References Cited

U.S. PATENT DOCUMENTS 1,901,143  3/1933  Brunner ............................... 285/382
3,831,629  8/1974  Mackal et al. ........................ 137/535

Primary Examiner—Alan Cohan

[57] ABSTRACT

Check valve adapted for being mounted in and sealed to a tube made of elastomeric material. The valve has an elongated outer hollow body made of thermoplastic material, said body being adapted to be telescoped for a substantial portion of its length into the end of the elastomeric tube. The valve is retained in the tube and sealed thereto by a formation comprising a flange having a first radially outwardly directed transverse portion integrally connected to the main part of the body of the valve and a second sleeve-like part coaxial of the main portion of the valve body, spaced from the outer surface thereof, and integrally connected at one of its ends to the outer edge of the first portion of the flange, the main portion of the body of the valve and the second portion of the flange forming an annular space adapted to receive the end of the tube therewithin, the outer free end of the second part of the flange being adapted to be deformed by being heated and thrust radially inwardly so as to secure the tube and seal it to the valve body.

2 Claims, 5 Drawing Figures

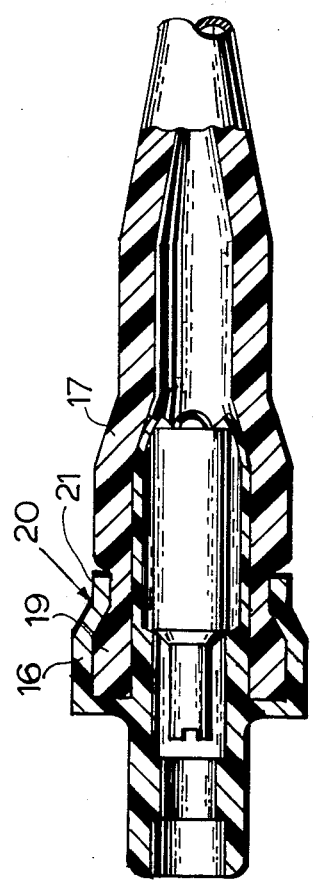
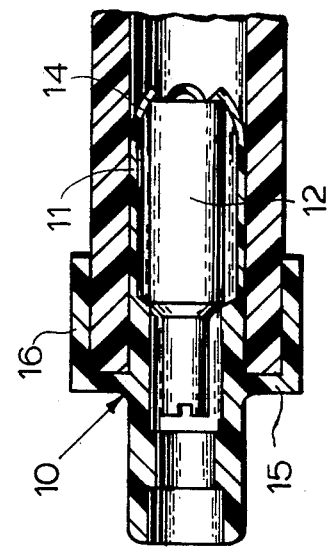
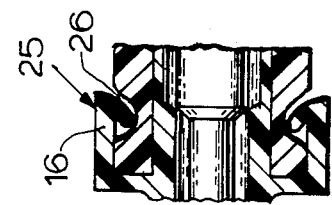
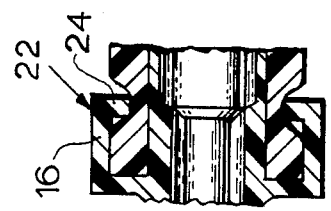
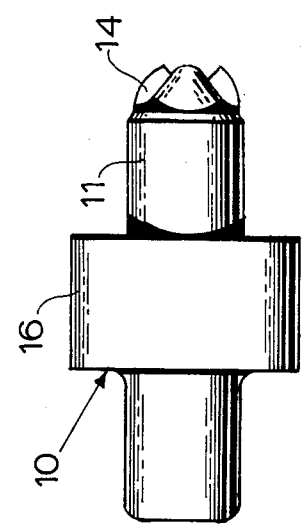

SELF-RETAINING CHECK VALVE AND MOUNTING THEREFOR

This invention relates to a valve such as a check valve having a body which incorporates a means integral therewith for retaining the check valve in and sealing it to an elastomeric tube. This simplifies the construction of the valve and its retainer, and in the case of a simple, two-piece check valve, keeps the number of pieces of the valve at two, while adding the additional feature of an integral retainer. The invention also relates to the combination of a valve and elastomeric tube in which the valve is mounted.

A typical use of the above-referred to two-piece check valve is that as a catheter valve. One such check valve is shown in U.S. Pat. No. 3,831,629 of Mackal et al. As shown in such patent, the catheter valve is retained in a rubber tube with a strong cylinder of rubber or vinyl which is stretched over the tube, thus clamping the rubber tube of the catheter to the valve. Other methods of retaining catheter valves in rubber tubes include the use of collet-type retainers, and the gluing of the valve body to the catheter tube. The rubber cylinder method of retention has the disadvantage of requiring substantial amounts of labor in its assembly, and not being aesthetically pleasing. The collet-type retainer requires an additional piece, and has to be sized to the catheter tube.

The disadvantages of the above-described prior art valve and its manner of being mounted in a rubber or elastomeric tube are overcome by the valve of the present invention wherein the tube retaining and sealing means is made as an integral part of the outer body of the valve.

The invention will be more readily understood upon consideration of the accompanying drawings, in which:

FIG. 1 is a view in side elevation of the valve of the invention;

FIG. 2 is a view in longitudinal axial section through such valve and the end of a rubber tube mounted thereon, the parts being shown in their position before the tube retaining means of the valve has been crimped;

FIG. 3 is a view similar to FIG. 2 but showing the tube retaining means of the valve after it has been crimped in accordance with the first embodiment of valve and tube connecting means of the invention;

FIG. 4 is a fragmentary view similar to a part of FIG. 3 in the vicinity of tube retaining means, such figure showing a second embodiment of crimping of the tube retaining and sealing means; and FIG. 5 is a view similar to FIG. 4 but showing a third embodiment of the crimping of the tube retaining and sealing means.

Turning first to FIG. 1, the check valve 10 there shown generally resembles that shown in the above-referred to Pat. No. 3,831,629 in so far as the main portion 11 of the valve body and the inner movable valve element 12 are concerned. The essential difference between the valve shown in the patent, and above-described as being typical of the prior art, and the valve of the present invention is that mounted upon the main part 11 of the valve body and preferably molded integrally therewith is an annular transverse flange 15 to which there is integrally connected the end of an outer sleeve 16 which lies radially spaced from the outer surface of the main part 11 of the valve body. The radial thickness of the annular space between part 11 and the part 16 of the valve body is such as fairly snugly to receive the end 19 of an elastomeric (rubber or rubber-like) tube 17 as shown in FIG. 2.

Such end 19 of tube 17 can be firmly attached to the valve and sealed thereto in any one of a number of ways, of which three are shown in FIGS. 3, 4 and 5, respectively. In all of such methods, when the valve body and sleeve are made of a plastic material having a very good memory, such as polypropylene, the free end of the sleeve 16 is heated to render it plastic and such free end is then deformed or crimped so as to decrease the diameter of such outer free end of the sleeve. This is done by applying suitable split dies to such outer end of the sleeve after it has been heated. It is to be understood that such dies may themselves have a heating means.

In FIG. 3 the dies deform the outer end of the sleeve 16 so as to form a short outer circular cylindrical portion of the sleeve of reduced diameter, such portion being joined to the main portion of the sleeve by an inclined junction section. The inwardly deformed outer free end of the sleeve deforms the end 19 of the tube 17 and is in forcible engagement therewith, whereby to prevent the tube from detachment from the valve and to provide an effective seal between them.

In FIG. 4 the outer end portion of the sleeve 16 is curled radially inwardly so as to present a radially narrow annular portion which lies in a plane disposed transversely of the tube and valve body as shown at 24 in FIG. 4.

In FIG. 5 the outer free end of the sleeve 16 is shown as having been deformed and thrust to the left, so that there is produced an annular portion 26 at the free end of the sleeve 16, annular portion 26 having the shape of a frustum of a cone which converges toward the left.

The outer body of the valve is made of a strong hard thermoplastic material, such as polypropylene, mentioned above, or rigid vinyl. It is to be noted that rigid vinyl deforms nicely in the crimping die without the addition of heat.

Although the invention is illustrated and described with reference to a plurality of embodiments thereof, it is to be expressly understood that it is in no way limited to the disclosure of such preferred embodiments but is capable of numerous modifications within the scope of the appended claims.

I claim:

1. In a check valve adapted for being mounted in and sealed to a tube made of elastomeric material, said valve comprising an elongated outer hollow body made of thermoplastic material, said body being adapted to be telescoped for a substantial portion of its length into the end of the elastomeric tube, the improvement comprising means integral with the valve body for retaining the valve in the tube and sealing it thereto comprising a flange having a first radially outwardly directed transverse portion integrally connected to the main part of the body of the valve and a second sleeve-like part coaxial of the main portion of the valve body, spaced from the outer surface thereof, and integrally connected at one of its ends to outer edge of the first portion of the flange, the main portion of the body of the valve and the second portion of the flange forming an annular space adapted to receive the end of the tube therewithin, the outer free end of the second part of the flange being adapted to be deformed by being thrust radially inwardly so as to secure the tube and seal it to the valve body, and an elastomeric tube within an end of which the valve is partially telescoped and sealed thereto, wherein the outer free end of the second part of the flange on the valve body has been heat deformed to form a radially inwardly extending annular portion thereof which presses inwardly and deforms the portion of the tube which it engages so as to thrust such zone of the tube strongly radially inwardly into sealing engagement with the outer surface of the main portion of the body of the valve, wherein said deformed outer end of the second part of the flange is in the form of a third annular flange attached to the outer end of the second part of the flange and extending radially inwardly therefrom, wherein said deformed outer end of the second part of the flange is in the form of a third annular flange attached to the outer end of the second part of the flange and extending radially inwardly therefrom.

2. In a check valve adapted for being mounted in and sealed to a tube made of elastomeric material, said valve comprising an elongated outer hollow body made of thermoplastic material, said body being adapted to be telescoped for a substantial portion of its length into the end of the elastomeric tube, the improvement comprising means integral with the valve body for retaining the valve in the tube and sealing it thereto comprising a flange having a first radially outwardly directed transverse portion integrally connected to the main part of the body of the valve and a second sleeve-like part coaxial of the main portion of the valve body, spaced from the outer surface thereof, and integrally connected at one of its ends to the outer edge of the first portion of the flange, the main portion of the body of the valve and the second portion of the flange forming an annular space adapted to receive the end of the tube therewithin, the outer free end of the second part of the flange being adapted to be deformed by being thrust radially inwardly so as to secure the tube and seal it to the valve body, and an elastomeric tube within an end of which the valve is partially telescoped and sealed thereto, wherein the outer free end of the second part of the flange on the valve body has been heat deformed to form a radially inwardly extending annular portion thereof which presses inwardly and deforms the portion of the tube which it engages so as to thrust such zone of the tube strongly radially inwardly into sealing engagement with the outer surface of the main portion of the body of the valve, wherein the deformed outer end of the second part of the flange, in addition to extending generally radially inwardly from the outer end of the second part of the flange also is of generally frusto-conical shape converging radially inwardly toward the first part of said flange.

* * * * *

UNITED STATES PATENT AND TRADEMARK OFFICE
CERTIFICATE OF CORRECTION

PATENT NO. : 4,602,655
DATED : 07/29/1986
INVENTOR(S) : Glen H. MACKAL

It is certified that error appears in the above-identified patent and that said Letters Patent are hereby corrected as shown below:

In Claim 1, column 3, lines 12-15 of the Patent, delete ", wherein said deformed outer end of the second part of the flange is in the form of a third annular flange attached to the outer end of the second part of the flange and extending radially inwardly therefrom." and substitute -- . -- therefor.

In Claim 1, column 2, line 47 of the Patent, delete "In" and substitute -- A combination of -- therefor.

In Claim 2, column 3, line 16 of the Patent, delete "In" and substitute -- A combination of -- therefor.

Signed and Sealed this

Twenty-ninth Day of September, 1987

Attest:

DONALD J. QUIGG

*Attesting Officer*  *Commissioner of Patents and Trademarks*